United States Patent
Ujihara et al.

(10) Patent No.: US 10,023,884 B2
(45) Date of Patent: Jul. 17, 2018

(54) MICROORGANISM PRODUCING DOCOSAHEXAENOIC ACID AND UTILIZATION THEREOF

(71) Applicant: KYOWA HAKKO BIO CO., LTD., Chiyoda-ku, Tokyo (JP)

(72) Inventors: Tetsuro Ujihara, Chiyoda-ku (JP); Megumi Nagano, Chiyoda-ku (JP); Kazuhiko Tabata, Chiyoda-ku (JP)

(73) Assignee: KYOWA HAKKO BIO CO., LTD., Tokyo (JP)

(*) Notice: Subject to any disclaimer, the term of this patent is extended or adjusted under 35 U.S.C. 154(b) by 118 days.

(21) Appl. No.: 14/760,290

(22) PCT Filed: Jan. 17, 2014

(86) PCT No.: PCT/JP2014/050753
§ 371 (c)(1),
(2) Date: Jul. 10, 2015

(87) PCT Pub. No.: WO2014/112574
PCT Pub. Date: Jul. 24, 2014

(65) Prior Publication Data
US 2015/0353972 A1    Dec. 10, 2015

(30) Foreign Application Priority Data
Jan. 18, 2013 (JP) .................. 2013-007006

(51) Int. Cl.
*C12P 7/64* (2006.01)
*C12R 1/89* (2006.01)
*C12N 1/12* (2006.01)

(52) U.S. Cl.
CPC .............. *C12P 7/6427* (2013.01); *C12N 1/12* (2013.01); *C12P 7/6472* (2013.01); *C12R 1/89* (2013.01)

(58) Field of Classification Search
None
See application file for complete search history.

(56) References Cited

U.S. PATENT DOCUMENTS 6,582,941 B1    6/2003    Yokochi et al.
7,259,006 B2    8/2007    Komazawa et al.
(Continued)

FOREIGN PATENT DOCUMENTS

JP    5-503425    6/1993
JP    8-502405    3/1996
(Continued)

OTHER PUBLICATIONS

English Translation of the Written Opinion of the ISA in PCT/JP2014/050753, dated Feb. 10, 2014.*
(Continued)

*Primary Examiner* — Richard C Ekstrom
(74) *Attorney, Agent, or Firm* — Fitzpatrick Cella Harper and Scinto

(57) ABSTRACT

According to the present invention, a microorganism belonging to the genus *Aurantiochytrium* having an 18S rRNA gene consisting of the base sequence represented by any of SEQ ID NOS: 1 to 5; *Aurantiochytrium* sp. OH4 strain; a microorganism which is a mutant obtained from the above-mentioned microorganism as a parent strain and has a higher ability to produce DHA than the parent strain; or *Aurantiochytrium* sp. LTR23 strain is provided. Also, a method for producing a DHA-containing composition, DHA and DHA alkyl ester by a fermentation process using the above-mentioned microorganisms is provided.

5 Claims, 2 Drawing Sheets

(56) References Cited

U.S. PATENT DOCUMENTS

| | | | |
|---|---|---|---|
| 2001/0046691 | A1 | 11/2001 | Bailey et al. |
| 2005/0019880 | A1* | 1/2005 | Raghukumar ........ C12P 7/6472 435/134 |
| 2009/0004219 | A1* | 1/2009 | Kallenmareth ...... A23C 15/126 424/195.17 |
| 2013/0089901 | A1 | 4/2013 | Seo et al. |
| 2013/0217084 | A1* | 8/2013 | Wen ...................... C12P 7/6427 435/134 |
| 2013/0288327 | A1 | 10/2013 | Watanabe et al. |
| 2015/0037838 | A1* | 2/2015 | Romari ..................... C12R 1/89 435/67 |

FOREIGN PATENT DOCUMENTS

| | | |
|---|---|---|
| JP | 8-509355 | 10/1996 |
| JP | 9-000284 | 1/1997 |
| JP | 10-072590 | 3/1998 |
| JP | 10-310556 | 11/1998 |
| JP | 2004-501603 | 1/2004 |
| JP | 2005-102680 | 4/2005 |
| JP | 2006-230403 | 9/2006 |
| WO | 1991/07498 | 5/1991 |
| WO | 1991/11918 | 8/1991 |
| WO | 1994/08467 | 4/1994 |
| WO | 2001/54510 | 8/2001 |
| WO | 2007/068997 | 6/2007 |
| WO | 2011/139040 | 11/2011 |
| WO | 2012/077799 | 6/2012 |
| WO | 2012/175027 | 12/2012 |

OTHER PUBLICATIONS

Hong, et al., "Production of Lipids Containing High Levels of Docosahexaeoic Acid by a Newly Isolated Microalga, *Aurantiochytrium* sp. KRS101", Appl Biochem Biotechnol, vol. 164, No. 8 (2011) 1468-80.

Harrington, et al., "The Polyunsaturated Fatty Acids of Marine Dinoflagellates", J. Protozool., vol. 17, No. 2 (1970) 213-19.

Sijtsma, et al., "Alternative Carbon Sources for Heterotrophic Production of Docosahexaenoic Acid by the Marine Alga *Crypthecodinium cohnii*", Single Cell Oils AOCS Press, Chapter 8 (2005) 107-23.

Wynn, et al., "Production of Single Cell Olls by Dinoflagellates", Single Cell Oils AOCS Press, Chapter 6 (2005) 86-98.

Yang, et al., "Isolation and Characterization of Taiwanese Heterotrophic Microalgae: Screening of Strains for Docosahexaenoic Acid (DHA) Production", Mar. Biotechnol., vol. 12 (2010) 173-85.

Yokochi, et al., "Optimization of docosahexaenoic acid production by Schizochytrium limacinum SR21", Appl. Microbial. Biotechnol., vol. 49 (1998) 72-6.

* cited by examiner

SEQUENCE LISTING

```
<160> NUMBER OF SEQ ID NOS: 7

<210> SEQ ID NO 1
<211> LENGTH: 1672
<212> TYPE: DNA
<213> ORGANISM: Aurantiochytrium sp.
```

<220> FEATURE:
<221> NAME/KEY: gene
<222> LOCATION: (1)..(1672)

<400> SEQUENCE: 1

```
tctggttgat cctgccagta gtcatatgct cgtctcaaag attaagccat gcatgtgtaa      60
gtataagcga ttgtactgtg agactgcgaa cggctcatta tatcagtaat aatttcttcg     120
gtagtttctt ttatatggat acctgcagta attctggaaa taatacatgc tgtaagagcc     180
ctgtatgggg ctgcacttat tagattgaag ccgatttat tggtgaatca tgataattga     240
gcagattgac tattttgtcg atgaatcgtt tgagttctg ccccatcagt tgtcgacggt      300
agtgtattgg actacggtga ctataacggg tgacggagag ttagggctcg actccggaga     360
gggagcctga gagacggcta ccatatccaa ggatagcagc aggcgcgtaa attacccact     420
gtggactcca cgaggtagtg acgagaaata tcgatgcgag gcgtgtatgc gttttgctat     480
cggaatgaga gcaatgtaaa accctcatcg aggatcaact ggagggcaag tctggtgcca     540
gcagccgcgg taattccagc tccagaagca tatgctaaag ttgttgcagt taaaaagctc     600
gtagttgaat ttctggcatg ggcgaccggt gctttccctg aatggggatt gattgtctgt     660
gttgccttgg ccatctttt cttttcttta ttgatgagaa atctttcact gtaatcaaag      720
cagagtgttc caagcaggtc gtatgaccgg tatgtttatt atgggatgat aagataggac     780
ttgggtgcta ttttgttggt ttgcacgcct gagtaatggt taataggaac agttgggggt     840
attcgtattt aggagctaga ggtgaaattc ttggatttcc gaaagacgaa ctagagcgaa     900
ggcatttacc aagcatgttt tcattaatca agaacgaaag tctggggatc gaagatgatt     960
agataccatc gtagtctaga ccgtaaacga tgccgacttg cgattgttgg gtgcttttt    1020
atgggcctca gcagcagcac atgagaaatc aaagtctttg ggttccgggg ggagtatggt    1080
cgcaaggctg aaacttaaag gaattgacgg aagggcacca ccaggagtgg agcctgcggc    1140
ttaatttgac tcaacacggg aaaacttacc aggtccagac ataggtagga ttgacagatt    1200
gagagctctt tcatgattct atgggtggtg gtgcatggcc gttcttagtt ggtggagtga    1260
tttgtctggt taattccgtt aacgaacgag acctcggcct actaaatagt gcgtggtatg    1320
gcaacatagt gcgttttaac ttcttagagg gacatgtccg gtttacgggc aggaagttcg    1380
aggcaataac aggtctgtga tgcccttaga tgttctgggc cgcacgcgcg ctacactgat    1440
gggttcatcg ggttttaatt ctattttttg gaattgagtg cttggtcgga aggcctggct    1500
aatccttgga acgctcatcg tgctggggct agattttgc aattattaat ctccaacgag    1560
gaattcctag taaacgcaag tcatcagctt gcattgaata cgtccctgcc ctttgtacac    1620
accgcccgtc gcacctaccg attgaacggt ccgatgaaac catgggatgt tt           1672
```

<210> SEQ ID NO 2
<211> LENGTH: 1672
<212> TYPE: DNA
<213> ORGANISM: Aurantiochytrium sp.
<220> FEATURE:
<221> NAME/KEY: gene
<222> LOCATION: (1)..(1672)

<400> SEQUENCE: 2

```
tctggttgat cctgccagta gtcatatgct cgtctcaaag attaagccat gcatgtgtaa      60
gtataagcga ttgtactgtg agactgcgaa cggctcatta tatcagtaat aatttcttcg     120
gtagtttctt ttatatggat acctgcagta attctggaaa taatacatgc tgtaagagcc     180
```

| | |
|---|---:|
| ctgtatgggg ctgcacttat tagattgaag ccgatttat tggtgaatca tgataattga | 240 |
| gcagattgac tttttttgtcg atgaatcgtt tgagtttctg ccccatcagt tgtcgacggt | 300 |
| agtgtattgg actacggtga ctataacggg tgacggagag ttagggctcg actccggaga | 360 |
| gggagcctga gagacggcta ccatatccaa ggatagcagc aggcgcgtaa attacccact | 420 |
| gtggactcca cgaggtagtg acgagaaata tcgatgcgag gcgtgtatgc gttttgctat | 480 |
| cggaatgaga gcaatgtaaa accctcatcg aggatcaact ggagggcaag tctggtgcca | 540 |
| gcagccgcgg taattccagc tccagaagca tatgctaaag ttgttgcagt taaaaagctc | 600 |
| gtagttgaat ttctggcatg ggcgaccggt gctttccctg aatggggatt gattgtctgt | 660 |
| gttgccttgg ccatctttt cttttcttta ttgatgagaa atctttcact gtaatcaaag | 720 |
| cagagtgttc caagcaggtc gtatgaccgg tatgtttatt atgggatgat aagataggac | 780 |
| ttgggtgcta ttttgttggt ttgcacgcct gagtaatggt taataggaac agttggggt | 840 |
| attcgtattt aggagctaga ggtgaaattc ttggatttcc gaaagacgaa ctagagcgaa | 900 |
| ggcatttacc aagcatgttt tcattaatca agaacgaaag tctggggatc gaagatgatt | 960 |
| agataccatc gtagtctaga ccgtaaacga tgccgacttg cgattgttgg gtgctttttt | 1020 |
| atgggcctca gcagcagcac atgagaaatc aaagtctttg ggttccgggg ggagtatggt | 1080 |
| cgcaaggctg aaacttaaag gaattgacgg aagggcacca ccaggagtgg agcctgcggc | 1140 |
| ttaattgac tcaacacggg aaaacttacc aggtccagac ataggtagga ttgacagatt | 1200 |
| gagagctctt tcatgattct atgggtggtg gtgcatggcc gttcttagtt ggtggagtga | 1260 |
| tttgtctggt taattccgtt aacgaacgag acctcggcct actaaatagt gcgtggtatg | 1320 |
| gcaacatagt gcgttttaac ttcttagagg acatgtccg gtttacgggc aggaagttcg | 1380 |
| aggcaataac aggtctgtga tgcccttaga tgttctgggc cgcacgcgcg ctacactgat | 1440 |
| gggttcatcg ggttttaatt ctatttttg gaattgagtg cttggtcgga aggcctggct | 1500 |
| aatccttgga acgctcatcg tgctggggct agatttttgc aattattaat ctccaacgag | 1560 |
| gaattcctag taaacgcaag tcatcagctt gcattgaata cgtccctgcc ctttgtacac | 1620 |
| accgcccgtc gcacctaccg attgaacggt ccgatgaaac catgggatgt tt | 1672 |

<210> SEQ ID NO 3
<211> LENGTH: 1673
<212> TYPE: DNA
<213> ORGANISM: Aurantiochytrium sp.
<220> FEATURE:
<221> NAME/KEY: gene
<222> LOCATION: (1)..(1673)

<400> SEQUENCE: 3

| | |
|---|---:|
| tctggttgat cctgccagta gtcatatgct cgtctcaaag attaagccat gcatgtgtaa | 60 |
| gtataagcga ttgtactgtg agactgcgaa cggctcatta tatcagtaat aatttcttcg | 120 |
| gtagtttctt ttatatggat acctgcagta attctgaaaa taatacatgc tgtaagagcc | 180 |
| ctgtatgggg ctgcacttat tagattgaag ccgatttat tggtgaatca tgataattga | 240 |
| gcagattgac tatttttgtc gatgaatcgt ttgagtttct gccccatcag ttgtcgacgg | 300 |
| tagtgtattg gactacggtg actataacgg gtgacggaga gttagggctc gactccggag | 360 |
| agggagcctg agacggct accatatcca aggatagcag caggcgcgta aattacccac | 420 |
| tgtggactcc acgaggtagt gacgagaaat atcgatgcga ggcgtgtatg cgttttgcta | 480 |
| tcggaatgag agcaatgtaa aaccctcatc gaggatcaac tggagggcaa gtctggtgcc | 540 |

```
agcagccgcg gtaattccag ctccagaagc atatgctaaa gttgttgcag ttaaaaagct      600
cgtagttgaa tttctggcat gggcgaccgg tgctttccct gaatggggat tgattgtctg      660
tgttgccttg gccatctttt tcttttcttt attgatgaga aatctttcac tgtaatcaaa      720
gcagagtgtt ccaagcaggt cgtatgaccg gtatgtttat tatgggatga taagatagga      780
cttgggtgct attttgttgg tttgcacgcc tgagtaatgg ttaataggaa cagttggggg      840
tattcgtatt taggagctag aggtgaaatt cttggatttc cgaaagacga actagagcga      900
aggcatttac caagcatgtt ttcattaatc aagaacgaaa gtctgggat cgaagatgat       960 tagataccat cgtagtctag accgtaaacg atgccgactt gcgattgttg ggtgcttttt     1020
tatgggcctc agcagcagca catgagaaat caaagtcttt gggttccggg gggagtatgg     1080
tcgcaaggct gaaacttaaa ggaattgacg gaagggcacc accaggagtg gagcctgcgg     1140
cttaatttga ctcaacacgg gaaaacttac caggtccaga cataggtagg attgacagat     1200
tgagagctct ttcatgattc tatgggtggt ggtgcatggc cgttcttagt tggtggagtg     1260
atttgtctgg ttaattccgt taacgaacga gacctcggcc tactaaatag tgcgtggtat     1320
ggcaacatag tgcgttttaa cttcttagag ggacatgtcc ggtttacggg caggaagttc     1380
gaggcaataa caggtctgtg atgcccttag atgttctggg ccgcacgcgc gctacactga     1440
tgggttcatc gggttttaat tctattttt ggaattgagt gcttggtcgg aaggcctggc      1500
taatccttgg aacgctcatc gtgctggggc tagattttg caattattaa tctccaacga      1560
ggaattccta gtaaacgcaa gtcatcagct tgcattgaat acgtccctgc cctttgtaca     1620
caccgcccgt cgcacctacc gattgaacgg tccgatgaaa ccatgggatg ttt            1673

<210> SEQ ID NO 4
<211> LENGTH: 1674
<212> TYPE: DNA
<213> ORGANISM: Aurantiochytrium sp.
<220> FEATURE:
<221> NAME/KEY: gene
<222> LOCATION: (1)..(1674)

<400> SEQUENCE: 4
tctggttgat cctgccagta gtcatatgct cgtctcaaag attaagccat gcatgtgtaa       60
gtataagcga ttgtactgtg agactgcgaa cggctcatta tatcagtaat aatttcttcg      120
gtagtttctt ttatatggat acctgcagta attctggaaa taatacatgc tgtaagagcc      180
ctgtatgggg ctgcacttat tagattgaag ccgattttat tggtgaatca tgataattga      240
gcagattgac atttttagt cgatgaatcg tttgagtttc tgccccatca gttgtcgacg       300
gtagtgtatt ggactacggt gactataacg ggtgacggag agttagggct cgactccgga      360
gagggagcct gagagacggc taccatatcc aaggatagca gcaggcgcgt aaattaccca      420
ctgtggactc cacgaggtag tgacgagaaa tatcgatgcg aggcgtgtat gcgttttgct      480
atcggaatga gagcaatgta aaccctcatc gaggatcaa ctggagggca agtctggtgc       540
cagcagccgc ggtaattcca gctccagaag catatgctaa agttgttgca gttaaaaagc      600
tcgtagttga atttctggca tgggcgaccg gtgctttccc tgaatgggga ttgattgtct      660
gtgttgcctt ggccatcttt tcttttctt tattgatgag aaatctttca ctgtaatcaa       720
agcagagtgt tccaagcagg tcgtatgacc ggtatgttta ttatgggatg ataagatagg      780
acttgggtgc tattttgttg gtttgcacgc ctgagtaatg gttaatagga acagttgggg      840
gtattcgtat ttaggagcta gaggtgaaat tcttggattt ccgaaagacg aactagagcg      900
```

| | |
|---|---|
| aaggcattta ccaagcatgt tttcattaat caagaacgaa agtctgggga tcgaagatga | 960 |
| ttagatacca tcgtagtcta gaccgtaaac gatgccgact tgcgattgtt gggtgctttt | 1020 |
| ttatgggcct cagcagcagc acatgagaaa tcaaagtctt tgggttccgg ggggagtatg | 1080 |
| gtcgcaaggc tgaaacttaa aggaattgac ggaagggcac caccaggagt ggagcctgcg | 1140 |
| gcttaatttg actcaacacg ggaaaactta ccaggtccag acataggtag gattgacaga | 1200 |
| ttgagagctc tttcatgatt ctatgggtgg tggtgcatgg ccgttcttag ttggtggagt | 1260 |
| gatttgtctg gttaattccg ttaacgaacg agacctcggc ctactaaata gtgcgtggta | 1320 |
| tggcaacata gtgcgtttta acttcttaga gggacatgtc cggtttacgg gcaggaagtt | 1380 |
| cgaggcaata acaggtctgt gatgccctta gatgttctgg ccgcacgcg cgctacactg | 1440 |
| atgggttcat cgggttttaa ttctattttt tggaattgag tgcttggtcg gaaggcctgg | 1500 |
| ctaatccttg gaacgctcat cgtgctgggg ctagattttt gcaattatta atctccaacg | 1560 |
| aggaattcct agtaaacgca agtcatcagc ttgcattgaa tacgtccctg ccctttgtac | 1620 |
| acaccgcccg tcgcacctac cgattgaacg gtccgatgaa accatgggat gttt | 1674 |

<210> SEQ ID NO 5
<211> LENGTH: 1673
<212> TYPE: DNA
<213> ORGANISM: Aurantiochytrium sp.
<220> FEATURE:
<221> NAME/KEY: gene
<222> LOCATION: (1)..(1673)

<400> SEQUENCE: 5

| | |
|---|---|
| tctggttgat cctgccagta gtcatatgct cgtctcaaag attaagccat gcatgtgtaa | 60 |
| gtataagcga ttgtactgtg agactgcgaa cggctcatta tatcagtaat aatttcttcg | 120 |
| gtagtttctt ttatatggat acctgcagta attctggaaa taatacatgc tgtaagagcc | 180 |
| ctgtatgggg ctgcacttat tagattgaag ccgattttat tggtgaatca tgataattga | 240 |
| gcagattgac ttttttaagtc gatgaatcgt ttgagtttct gccccatcag ttgtcgacgg | 300 |
| tagtgtattg gactacggtg actataacgg gtgacggaga gttagggctc gactccggag | 360 |
| agggagcctg agagacggct accatatcca aggatagcag caggcgcgta aattacccac | 420 |
| tgtggactcc acgaggtagt gacgagaaat atcgatgcga ggcgtgtatg cgttttgcta | 480 |
| tcggaatgag agcaatgtaa aaccctcatc gaggatcaac tggagggcaa gtctggtgcc | 540 |
| agcagccgcg gtaattccag ctccagaagc atatgctaaa gttgttgcag ttaaaaagct | 600 |
| cgtagttgaa tttctggcat gggcgaccgg tgctttccct gaatgggat tgattgtctg | 660 |
| tgttgccttg gccatctttt tcttttcttt attgatgaga atctttcac tgtaatcaaa | 720 |
| gcagagtgtt ccaagcaggt cgtatgaccg gtatgtttat tatgggatga taagatagga | 780 |
| cttgggtgct attttgttgg tttgcacgcc tgagtaatgg ttaataggaa cagttggggg | 840 |
| tattcgtatt taggagctag aggtgaaatt cttggatttc cgaaagacga actagagcga | 900 |
| aggcatttac caagcatgtt ttcattaatc aagaacgaaa gtctggggat cgaagatgat | 960 |
| tagataccat cgtagtctag accgtaaacg atgccgactt gcgattgttg ggtgctttt | 1020 |
| tatgggcctc agcagcagca catgagaaat caaagtcttt gggttccggg gggagtatgg | 1080 |
| tcgcaaggct gaaacttaaa ggaattgacg gaagggcacc accaggagtg gagcctgcgg | 1140 |
| cttaatttga ctcaacacgg gaaaacttac caggtccaga cataggtagg attgacagat | 1200 |
| tgagagctct ttcatgattc tatgggtggt ggtgcatggc cgttcttagt tggtggagtg | 1260 |

```
atttgtctgg ttaattccgt taacgaacga gacctcggcc tactaaatag tgcgtggtat    1320
ggcaacatag tgcgttttaa cttcttagag ggacatgtcc ggtttacggg caggaagttc    1380
gaggcaataa caggtctgtg atgcccttag atgttctggg ccgcacgcgc gctacactga    1440
tgggttcatc gggttttaat tctattttt ggaattgagt gcttggtcgg aaggcctggc     1500
taatccttgg aacgctcatc gtgctggggc tagattttg caattattaa tctccaacga     1560
ggaattccta gtaaacgcaa gtcatcagct tgcattgaat acgtccctgc cctttgtaca    1620
caccgcccgt cgcacctacc gattgaacgg tccgatgaaa ccatgggatg ttt           1673

<210> SEQ ID NO 6
<211> LENGTH: 23
<212> TYPE: DNA
<213> ORGANISM: Artificial Sequence
<220> FEATURE:
<223> OTHER INFORMATION: Synthetic DNA

<400> SEQUENCE: 6
tctggttgat cctgccagta gtc                                              23

<210> SEQ ID NO 7
<211> LENGTH: 25
<212> TYPE: DNA
<213> ORGANISM: Artificial Sequence
<220> FEATURE:
<223> OTHER INFORMATION: Synthetic DNA

<400> SEQUENCE: 7
aaacatccca tggtttcatc ggacc                                            25
```

MICROORGANISM PRODUCING DOCOSAHEXAENOIC ACID AND UTILIZATION THEREOF

This application is a national phase of PCT Application No. PCT/JP2014/050753 filed Jan. 17, 2014, which in turn claims benefit of Japanese Application No. 2013-007006 filed Jan. 18, 2013.

TECHNICAL FIELD

The present invention relates to a novel microorganism which produces docosahexaenoic acid (hereinafter referred to as "DHA"), and methods for producing a DHA-containing composition, DHA, and DHA alkyl ester using the microorganism.

BACKGROUND ART

DHA is a polyunsaturated fatty acid contained abundantly in phospholipids in the brain and the like of mammals including human beings and is known to play an important role in the maintenance or development of brain functions. Human beings have an ability to synthesize DHA from linolenic acid, however, the amount thereof is much smaller than the required amount, and it is known that DHA should be taken from an outside. For this reason, many foods, supplements, and milk for babies containing DHA are sold.

Examples of DHA contained in these products include DHA obtained by extraction from fish oils. Fish oils are inexpensive and rich in DHA, and therefore are good sources for DHA. However, in consideration of a recent increase in demand for DHA, accumulation of PCB or a heavy metal in fish accompanying marine pollution, etc., DHA to be supplied more safely and stably has been demanded.

Other than DHA obtained by extraction from fish oils, the examples include DHA produced by a fermentation method using a microorganism. It has been known for a long time that marine microalgae produce a lipid containing DHA (Non-Patent Document 1). However, there are problems that the amount of DHA contained in microalgae is small, high-density cultivation is difficult, etc., and therefore, production at a commercial level was not performed.

As a method for producing DHA by fermentation at a commercial level, the case using dinoflagellate *Cryptheco-dinium cohnii* is the first study to report the method (Patent Document 1 and Non-Patent Documents 2 and 3). Thereafter, multiple microorganisms having an ability to produce DHA were discovered, and microorganisms exhibiting the highest ability to produce DHA are Labyrinthulea microorganisms, and examples of such microorganisms include *Schizochytrium* sp. ATCC 20888 strain and derivative strains thereof (Patent Documents 2 and 3), *Aurantiochytrium limacinum* (formerly classified as *Schizochytrium limacinum*) SR21 strain (Patent Documents 4 to 6 and Non-Patent Document 4), Labyrinthulea microorganism 12B strain (Patent Document 7), *Thraustochytrium* sp. LEF strain (Patent Document 8), and the like.

Among these Labyrinthulea microorganisms, a microorganism exhibiting the highest ability to produce DHA is a *Schizochytrium* sp. S31 strain (ATCC 20888 strain) (Patent Document 9). The ability to produce DHA of the microorganism is overwhelmingly higher as compared with other reports, and a fermentation method for DHA using the microorganism can be said to be a fermentation production process with the lowest cost.

However, even with the fermentation production process, the cost is higher than with the extraction method from fish oils, and therefore, further improvement of productivity has been demanded.

RELATED ART DOCUMENTS

Patent Documents

Patent Document 1: JP-T-5-503425
Patent Document 2: JP-T-8-502405
Patent Document 3: JP-T-8-509355
Patent Document 4: JP-A-9-000284
Patent Document 5: JP-A-10-072590
Patent Document 6: JP-A-10-310556
Patent Document 7: JP-A-2006-230403
Patent Document 8: JP-A-2005-102680
Patent Document 9: JP-T-2004-501603

Non-Patent Documents

Non-Patent Document 1: J. Protozoal (1970), Vol. 17, pp. 213-219
Non-Patent Document 2: Single Cell Oils AOCS Press (2005), Vol. 6, pp. 86-98
Non-Patent Document 3: Single Cell Oils AOCS Press (2005), Vol. 8, pp. 107-123
Non-Patent Document 4: Appl. Microbiol. Biotechnol. (1998), Vol. 49, pp. 72-76

SUMMARY OF THE INVENTION

Problems to Be Solved by the Invention

An object of the present invention is to provide a microorganism having a higher ability to produce DHA than before, and also to provide efficient methods for producing a DHA-containing composition, DHA, and DHA alkyl ester using the microorganism.

Means for Solving the Problems

The present invention relates to the following [1] to [7].
[1] A microorganism belonging to the genus *Aurantiochytrium* having an 18S rRNA gene consisting of the base sequence represented by any of SEQ ID NOS: 1 to 5.
[2] *Aurantiochytrium* sp. OH4 strain (Accession Number: FERM BP-11524).
[3] A microorganism which is a mutant obtained from the microorganism described in [1] or [2] above as a parent strain and has a higher ability to produce DHA than the parent strain.
[4] *Aurantiochytrium* sp. LTR23 strain.
[5] A method for producing a DHA-containing composition comprising culturing the microorganism described in any one of [1] to [4] above in a medium, allowing the DHA-containing composition to be produced and accumulated in a culture, and collecting the DHA-containing composition from the culture.
[6] A method for producing DHA comprising separating and collecting DHA from the DHA-containing composition collected in [5] above.
[7] A method for producing DHA alkyl ester comprising separating and collecting DHA alkyl ester from the DHA-containing composition collected in [5] above.

Effects of the Invention

According to the present invention, a microorganism belonging to the genus *Aurantiochytrium* having an 18S rRNA gene consisting of the base sequence represented by any of SEQ ID NOS: 1 to 5, and a method for producing DHA-containing composition, DHA and DHA alkyl ester by a fermentation process using the microorganism are provided.

EMBODIMENTS FOR CARRYING OUT THE INVENTION

1. Microorganism of the Invention

Figure 1:
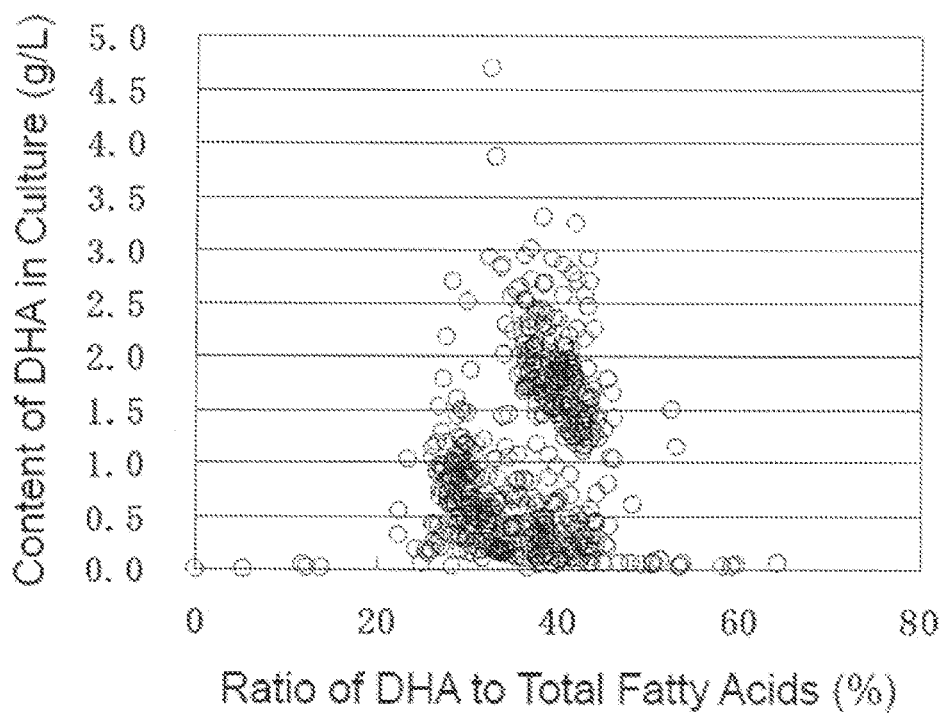
FIG. 1 is a view showing the production amounts of DHA and the ratios of DHA to the total fatty acids in DHA-producing microorganisms collected from a coastal area of Okinawa.

The microorganism of the present invention is a microorganism belonging to the genus *Aurantiochytrium* having one or more, preferably two or more, more preferably three or more, further more preferably four or more 18S rRNA genes, each consisting of the base sequence represented by any of SEQ ID NOS: 1 to 5, and is most preferably a microorganism belonging to the genus *Aurantiochytrium* having all the 18S rRNA genes consisting of base sequences represented by SEQ ID NOS: 1 to 5, respectively. Based on the morphological characteristics and the molecular biological characteristics as mentioned below, the microorganism of the present invention is considered to belong to the phyrum Heterokonta of the kingdom Chromista, and further belong to the order Labyrinthulida of the class Labyrinthulea. Regarding the taxonomic ranks of family and below, in consideration of the physiomorphological characteristics and the base sequences of 18S rRNA genes, it is considered to belong to the genus *Aurantiochytrium* of the family Thraustochytriaceae.

Examples of the microorganism of the present invention include an *Aurantiochytrium* sp. OH4 strain (Accession Number: FERM BP-11524) and the like. Further, microorganisms which are mutants obtained by using the microorganism of the present invention as a parent strain and have a higher ability to produce DHA than the parent strain are also included in the microorganism of the present invention. Examples of such a microorganism include an *Aurantiochytrium* sp. LTR23 strain, and the like.

The above-mentioned *Aurantiochytrium* sp. OH4 strain was deposited at the Patent Microorganisms Depositary of the National Institute of Technology and Evaluation (NITE) located at Central 6, 1-1, Higashi, Tsukuba-shi, Ibaraki-ken, Japan (postal code: 305-8566). The date of receipt (date of deposit) is Jan. 11, 2013, and the accession number is FERM BP-11524.

The parent strain as used herein refers to an original strain to be subjected to introduction of a mutation, gene replacement by a DNA recombination technique, or the like. The original strain to be subjected to gene replacement by a DNA recombination technique, or the like is also referred to as a host strain.

The mutant as used herein refers to a microorganism which can be obtained by using a conventional mutation introduction method, a gene replacement method through a DNA recombination technique, or the like from the microorganism of the present invention as a parent strain.

The microorganism which has a higher ability to produce DHA than the parent strain as used herein refers to a microorganism in which the amount of a DHA-containing composition or DHA capable of being obtained from the entire culture is large when the parent strain and the mutant are cultured under the same cultivation conditions.

Examples of the DHA-containing composition can include DHA-containing oils and fats or DHA-containing phospholipids, preferably DHA-containing oils and fats.

Many types of microorganisms belonging to the genus *Aurantiochytrium* have been found so far, however, the microorganism of the present invention is different in the base sequence of an 18S rRNA gene from these microorganisms, and also as shown in Examples mentioned below, the dry cell weight and the content of DHA when the microorganism is cultured are significantly higher than in the case of conventionally known microorganisms having been reported as DHA high-producing microorganisms, and therefore, the microorganism of the present invention can be clearly distinguished from the conventionally known microorganisms belonging to the genus *Aurantiochytrium*.

2. Method for Obtaining Microorganism of the Invention

The microorganism of the present invention can be obtained by the following method.

A sample is collected from the ocean, preferably from brackish water, most preferably from fallen leaves collected from a mangrove forest floor.

The sample is soaked in artificial seawater containing an antibiotic, preferably penicillin G and streptomycin, and thereafter, the supernatant of the artificial seawater is placed on an agar medium containing the antibiotic, and incubated for several days at 20 to 40° C., preferably at 25° C. By doing this, many prokaryotes present in the environment cannot grow, and therefore, the microorganism of the present invention, which is a eukaryote, can be concentrated.

A colony is isolated, and from the culture obtained by cultivation using a liquid medium, a genomic DNA is extracted according to a common procedure. By using the genomic DNA as a template, a PCR reaction is performed using oligo DNAs having the base sequences represented by SEQ ID NOS: 6 and 7, respectively, which can amplify an 81S rRNA gene, as a primer set.

Here, to one of the primers of the primer set, a tag composed of 3 to 6 bases, preferably 4 to 5 bases, most preferably 4 bases for simultaneously analyzing multiple samples is added according to "high-speed sequence analysis outsourcing service, Application No. 01, Analysis of 16S rRNA PCR sample" (Takara Bio, Inc. brochure). Further, to both primers, an oligonucleotide necessary for an analysis with GS FLX Sequencer (Roche Diagnostics K.K.) is added.

By performing sequence determination with GS FLX Sequencer using the above-mentioned PCR reaction product, for example, in the case where the size of the above-mentioned tag is set to 4 bases, and up to 256 types of tag sequences are used, 256 types of 18S rRNA genes can be sequenced by one sequencing operation without requiring a cloning operation. Specifically, by mixing 256 types of PCR products, the base sequences are determined with GS FLX Sequencer, and the base sequences after the determination are classified into 256 types by using the tag sequences as the index.

The genomic DNA to be used as the template for the PCR reaction may be a genomic DNA extracted from a single strain, or may be a mixture of genomic DNAs extracted from multiple strains. However, in the case of using a mixture of genomic DNAs extracted from multiple strains, screening of many strains can be more conveniently performed by combining the bellow-mentioned method.

For example, an 18S rRNA gene region is amplified by mixing genomic DNAs extracted from 100 types of strains and using the resulting mixture as a template for a PCR reaction, and also using the above-mentioned primer set.

The PCR products are sequenced with GS FLX Sequencer, and in the case where an 18S rRNA gene consisting of the base sequence represented by any of SEQ ID NOS: 1 to 5 is present, it is found that at least one strain of the microorganism of the present invention is present among the 100 types of strains. On the other hand, in the case where the 18S rRNA gene is not present, it is found that the microorganism of the present invention is not present among the 100 types of strains.

In the case where the microorganism of the present invention is present among the 100 types of strains, the microorganism can be specified using a method with the above-mentioned GS FLX Sequencer by one sequencing operation.

That is, by using the above-mentioned method, in the case where the size of the tag sequence is set to 4 bases, up to 256 types of mixed genomic DNAs can be analyzed by the first sequencing operation, and the microorganism of the present invention can be specified among up to 256 types of microorganisms by the second sequencing operation, and therefore, with respect to up to 65,536 types of microorganisms, it can be determined as to whether or not a microorganism is the microorganism of the present invention by only two sequencing operations without requiring a cloning operation.

Incidentally, in the case where the size of the tag sequence is set to 5 bases, up to 1,024 types of mixed genomic DNAs can be analyzed by the first sequencing operation, and the microorganism of the present invention can be specified among up to 1,024 types of microorganisms by the second sequencing operation, and therefore, with respect to up to 1,048,576 types of microorganisms, it can be determined as to whether or not a microorganism is the microorganism of the present invention by only two sequencing operations without requiring a cloning operation.

The microorganism to be subjected to the above sequencing analysis may be confirmed to produce DHA beforehand. By doing this, in the case where the number of strains to be analyzed is small, it can also be determined as to whether or not a microorganism is the microorganism of the present invention by sequence determination using the conventional Sanger method.

The mutant of the present invention having a higher ability to produce DHA than the parent strain can be obtained by using the microorganism of the present invention as a parent strain and using a conventional mutation treatment method, for example, a mutation treatment is performed such that the death rate of the microorganism is 98%, preferably 99%, most preferably 99.9% with an N-methyl-N'-nitro-N-nitrosoguanidine (NTG) treatment or a UV irradiation treatment, and a surviving colony is isolated and the productivity of DHA is examined.

The productivity of DHA can be examined by a method in which a lipid is extracted from a culture solution using the Bligh & Dyer method (Bligh E G and Dyer W J, Can. J. Biochem. Physiol. 37 911 (1959)) and dried under reduced pressure, and thereafter, the dried lipid is subjected to fatty acid methylation using the fatty acid methylation kit (Nacalai Tesque, Inc.), and the obtained fatty acid methyl ester is extracted with n-hexane and analyzed using gas chromatography.

3. Method for Producing DHA-Containing Composition of the Invention

A DHA-containing composition can be produced by culturing the microorganism of the present invention in a medium, allowing the DHA-containing composition to be produced and accumulated in the culture, and collecting the DHA-containing composition from the culture.

The culture of the microorganism of the present invention can be obtained by inoculating the microorganism into an appropriate medium and culturing the microorganism according to a common procedure.

As the medium, any known medium containing a carbon source, a nitrogen source, an inorganic salt, and the like can be used. Examples of the carbon source include a carbohydrate such as glucose, fructose, or galactose, and other than this, an oil or a fat such as oleic acid or soybean oil, glycerol, sodium acetate, or the like. These carbon sources can be used, for example, at a concentration of 20 to 300 g per liter of the medium. According to a particularly preferred embodiment, by feeding a carbon source after the initial carbon source is consumed, the cultivation can be continuously performed. By performing cultivation under such conditions, the amount of the carbon source to be consumed can be increased, and thus, the production amount of the DHA-containing composition can be increased.

Further, as the nitrogen source, organic nitrogen such as yeast extract, corn steep liquor, polypeptone, sodium glutamate, or urea, or inorganic nitrogen such as ammonium acetate, ammonium sulfate, ammonium chloride, sodium nitrate, ammonium nitrate, or ammonia can be used.

As the inorganic salt, potassium phosphate, or the like can be suitably combined and used.

It is preferred that the medium containing the above-mentioned respective components is used by sterilization in an autoclave after adjusting the pH in a range of 4.0 to 9.5 by adding an appropriate acid or base.

The cultivation temperature is generally from 10 to 45° C., preferably from 20 to 37° C. The cultivation temperature is preferably controlled to be a cultivation temperature at which a DHA-containing composition can be produced. The pH during cultivation is generally from 3.5 to 9.5, preferably 4.5 to 9.5. A particularly preferred pH varies depending on the intended purpose, and in order to produce a large amount of an oil or fat, the pH is from 5.0 to 8.0.

The cultivation period can be set to, for example 2 to 7 days, and the cultivation can be performed by aeration agitation cultivation or the like.

By culturing the microorganism of the present invention as described above, a culture containing the microorganism in an amount of generally from 50 to 200 g, preferably from 100 to 200 g in terms of dry cell weight per liter of the medium can be obtained.

As a method for separating the culture solution and the microorganisms from the culture, a conventional method known to those skilled in the art can be performed, and for example, the separation can be performed by a centrifugation method, filtration, or the like.

The microorganisms separated from the culture are homogenized by, for example, ultrasound, a DYNO-MILL, or the like, and thereafter, for example, solvent extraction is performed with chloroform, hexane, butanol, or the like, whereby a DHA-containing composition can be obtained.

By the method for producing a DHA-containing composition of the present invention, the DHA-containing composition can be obtained in an amount of 5 to 100 g, preferably 10 to 80 g per 100 g of dry cell weight.

The DHA-containing composition to be produced by the above-mentioned production method is subjected to, for example, a method such as a low-temperature solvent fractionation method [Koretaro Takahashi, Journal of Japan Oil Chemist's Society, 40: 931-941 (1991)] or a method of liberating and removing short-chain fatty acids with a hydrolase such as lipase [Koretaro Takahashi, Journal of Japan Oil Chemist's Society, 40: 931-941 (1991)], to concentrate the DHA-containing composition, whereby a DHA-containing composition having a high DHA content can be obtained.

4. Method for Producing DHA of the Invention

The method for producing DHA of the present invention is characterized by separating and collecting DHA from the DHA-containing composition obtained by the production method described in the above 3.

The separation and collection of DHA from the DHA-containing composition can be performed by preparing mixed fatty acids containing DHA from the DHA-containing composition by, for example, a hydrolysis method, and thereafter separating and collecting DHA by, for example, a urea addition method, a cooling separation method, high-performance liquid chromatography, supercritical chromatography, or the like.

5. Method for Producing DHA Alkyl Ester of the Invention

The method for producing DHA alkyl ester of the present invention is characterized by separating and collecting DHA alkyl ester from the DHA-containing composition obtained by the production method described in the above 3.

The DHA alkyl ester is not particularly limited as long as it is DHA alkyl ester, however, examples thereof include preferably DHA methyl ester or DHA ethyl ester, more preferably DHA ethyl ester.

The separation and collection of the DHA alkyl ester from the DHA-containing composition can be performed by preparing mixed fatty acid alkyl esters containing DHA alkyl ester from the DHA-containing composition by, for example, an alcoholysis method, and thereafter separating and collecting the DHA alkyl ester by, for example, a urea addition method, a cooling separation method, high-performance liquid chromatography, supercritical chromatography, or the like.

Hereinafter, Examples of the Invention of this application will be shown, however, the present invention is not limited to these Examples.

Example 1

Acquisition of Microorganism of the Invention (1)

1. Isolation of Microorganism of the Invention

As a sample, from which the microorganism of the present invention is isolated, fallen leaves collected from a mangrove forest floor (a brackish water region) near a coastal area in Okinawa were used. The fallen leaves were soaked in artificial seawater containing penicillin G and streptomycin at 300 mg/L, and thereafter, the supernatant of the artificial seawater is placed on an agar medium for isolation containing penicillin G and streptomycin (each at 300 mg/L), and incubated at 25° C. for several days.

As the agar medium for isolation, an agar medium having the following composition: 0.2% glucose, 0.02% yeast extract, 50% artificial seawater, 0.05% sodium glutamate, and 1.5% agarose was used.

After the emergence of many colonies on the agar plate was confirmed, the colonies were separated and cultured in a liquid medium for evaluation at 30° C. for 48 hours.

As the liquid medium for evaluation, a liquid medium having the following composition: 9% glucose, 1% yeast extract, 1% peptone, and 50% artificial seawater was used.

From the culture solution, a lipid was extracted using the Bligh & Dyer method (Bligh E G and Dyer W J, Can. J. Biochem. Physiol. 37 911 (1959)) and dried under reduced pressure. Then, the dried lipid was subjected to fatty acid methylation using a fatty acid methylation kit (Nacalai Tesque, Inc.), and the fatty acid methyl ester obtained by this treatment was extracted with n-hexane. This fatty acid methyl ester was analyzed by gas chromatography, and the amount and composition of fatty acids in the culture solution were examined.

The conditions for the gas chromatography were set as follows.

Column: HR-SS-10 (Shinwa Chemical Industries Ltd.), 0.25 mm×25 m
Carrier gas: He, 30 mL/min
Column temperature: 190° C.
Detection: FID According to the above procedure, 1239 strains of DHA-producing microorganisms could be obtained from 5000 or more strains of mangrove-derived organisms.

The content of DHA and the ratio of DHA to the total fatty acids in the culture of each of the DHA-producing microorganisms obtained at this time are shown in FIG. 1. From FIG. 1, it is confirmed that there is a tendency that generally as the ratio of DHA is increased, the growth is deteriorated, so that the amount of total fatty acids is decreased and the content of DHA is decreased, and it was confirmed that the ratio of DHA in the strains which produce a large amount of fatty acids was concentrated on around 30% to 40% as it has been known so far. Among these, a strain which grows well and shows high DHA productivity was selected and named "OH4 strain".

2. Morphological Characteristics of OH4 Strain

The OH4 strain is unicellular and can grow in the presence of penicillin G and streptomycin, and therefore, it is concluded that the OH4 strain is a unicellular eukaryote. Further, based on the fact that the OH4 strain was isolated from a sample derived from the mangrove forest floor and that the content of DHA was very high, the OH4 strain was presumed to be a thraustochytrid belonging to Heteroconta.

Figure 2:
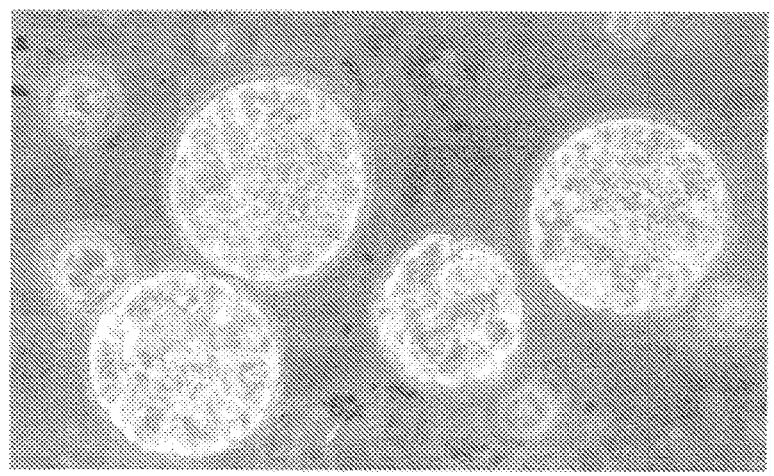
FIG. 2 is a photomicrograph of an *Aurantiochytrium* sp. OH4 strain.

In the OH4 strain, an ectoplasmic net extending from a spherical cell with a diameter of 10 to 20 μm could be observed in the above-mentioned agar medium for isolation, and therefore, it was confirmed that the OH4 strain belongs to the family Thraustochytriaceae of the class Labyrinthulea of the kingdom Chromista. Further, it was confirmed that vegetative cells have a spherical shape and proliferate by binary fission of microorganisms. Such a life history is characteristic of the genera *Aurantiochytrium* (Yokoyama R. et. al., Mycoscience 48: 329-341; Daisuke Honda, Phylogeny and Taxonomy of the Labyrinthula, Kaiyo to Seibutsu (Aquabiology), 23: 7-18, 2001). A photomicrograph of the OH4 strain is shown in FIG. 2.

3. Molecular Biological Characteristics of OH4 Strain

The OH4 strain cultured by using the above-mentioned liquid medium for evaluation in the logarithmic growth phase was recovered, and the total genomic DNA was extracted by a common procedure using glass beads and phenol-chloroform. A PCR reaction was performed using the obtained genomic DNA as a template, and oligonucleotides consisting of base sequences represented by SEQ ID NOS: 6 and 7, respectively as a primer set, and an 18S rRNA gene was amplified. The base sequence of the obtained PCR product was determined by the Sanger method.

Here, in the process of determining the base sequence of the 18S rRNA gene of the OH4 strain, it was found that the molecule is polymorphic. It is a conventionally known phenomenon that the sequence of the 18S rRNA gene of a Labyrinthulea microorganism is polymorphic (Patent Document 7). The base sequences of the 18S rRNA genes of the OH4 strain are represented by SEQ ID NOS: 1 to 5, respectively.

Further, differences in the respective polymorphic sequences are shown in Table 1. The base numbers are shown based on SEQ ID NO: 4 which is the longest sequence.

TABLE 1

Comparison of 18S rRNA Gene Sequences of OH4 Strain

| Base number | 250 | 251 | 252 | 253 | 254 | 255 | 256 | 257 | 258 | 259 |
|---|---|---|---|---|---|---|---|---|---|---|
| SEQ ID NO: 1 | C | - | T | - | A | T | T | T | T | G |
| SEQ ID NO: 2 | C | - | T | - | T | T | T | T | T | G |
| SEQ ID NO: 3 | C | - | T | A | T | T | T | T | T | G |
| SEQ ID NO: 4 | C | A | T | T | T | T | T | T | A | G |
| SEQ ID NO: 5 | C | - | T | T | T | T | T | A | A | G |

The base sequences represented by SEQ ID NOS: 1 to 5 were searched using the algorithm BLAST by Karlin and Altschul [Pro. Natl. Acad. Sci. USA, 90, 5873 (1993) (http://www.ncbi.nlm.nih.gov)]. As a result, these base sequences showed a 99% identity with the base sequences of the 18S rRNA genes of an *Aurantiochytrium* sp. KRS101 strain and an *Aurantiochytrium* sp. BL11 strain.

On the other hand, no sequences which completely match with any of the base sequences represented by SEQ ID NOS: 1 to 5 were found in the NCBI database.

Based on the above-mentioned morphological characteristics and molecular biological characteristics, it was concluded that the OH4 strain is a novel microorganism belonging to the genus *Aurantiochytrium* and named "*Aurantiochytrium* sp. OH4 strain", and deposited at the Patent Microorganisms Depositary of the National Institute of Technology and Evaluation (NITE) (Central 6, 1-1, Higashi, Tsukuba-shi, Ibaraki-ken, Japan) on Jan. 11, 2013 under the Accession Number of FERM BP-11524.

Incidentally, the classification may be changed by the progress of research in the future, however, the microorganism of the present invention is still a novel microorganism.

Example 2

Acquisition of Microorganism of the Invention (2)
1. Acquisition of Mutant obtained by using *Aurantiochytrium* sp. OH4 strain as Parent Strain The *Aurantiochytrium* sp. OH4 strain was subjected to a mutation treatment with N-methyl-N'-nitro-N-nitrosoguanidine (NTG) such that the death rate was 99.9%. Then, a surviving colony was isolated and cultured in a liquid medium for evaluation at 30° C. for 48 hours. As a result, a strain in which the ratio of DHA was increased to about 1.6 times, and accompanying this, the content of DHA was increased to about 3 times could be obtained. This strain was named "*Aurantiochytrium* sp. LTR23 strain".

Figure 3:
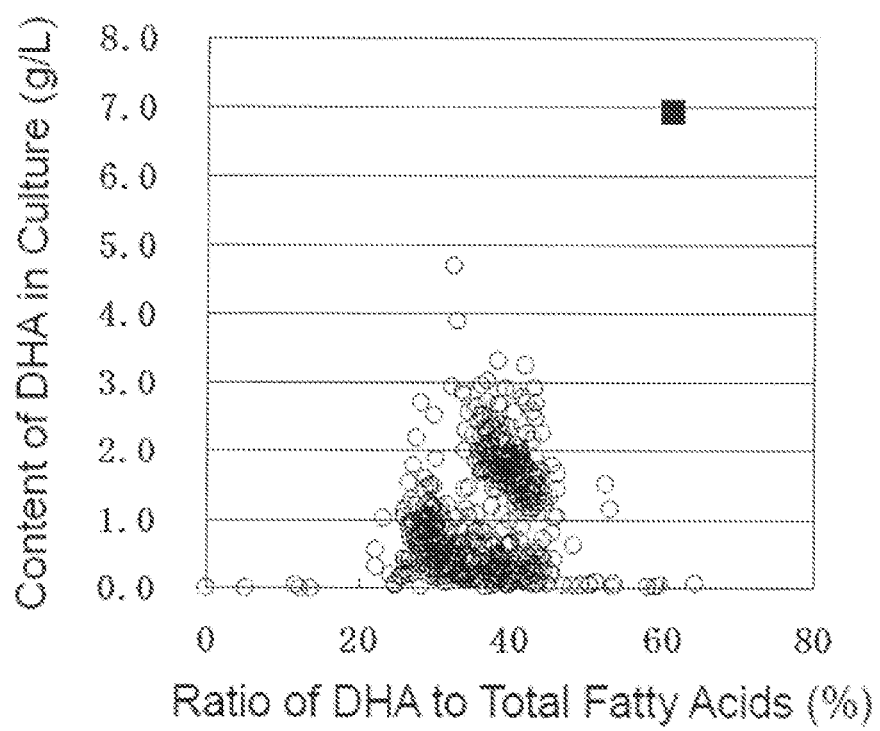
FIG. 3 is a view in which the production amount of DHA and the ratio of DHA to the total fatty acids in an *Aurantiochytrium* sp. LTR23 strain are added to FIG. 1.

FIG. 3 is a view in which the content of DHA and the ratio of DHA to the total fatty acids in the culture of the *Aurantiochytrium* sp. LTR23 strain are added to FIG. 1. From FIG. 3, it could be confirmed that the *Aurantiochytrium* sp. LTR23 strain has a higher DHA ratio and also has a higher DHA content even in comparison with a spontaneous isolate.

Example 3

Industrial Production of DHA-Containing Composition of the Invention
1. Cultivation of *Aurantiochytrium* sp. OH4 Strain and LTR23 Strain Each of the *Aurantiochytrium* sp. OH4 strain and LTR23 strain was cultured in a jar fermenter. Further, for comparison, *Aurantiochytrium limacinum* SR21 strain (Patent Documents 4 to 6 and Non-Patent Document 4) and *Schizochytrium* sp. S31 strain (Patent Document 9) having been reported as DHA high-producing microorganisms were cultured under the same conditions.

The *Aurantiochytrium limacinum* SR21 strain (ATCC MYA-1381) and the *Schizochytrium* sp. S31 strain (ATCC 20888) were obtained from American Type Culture Collection (ATCC).

Each of the above-mentioned cryopreserved microbial strains was inoculated onto the agar medium for isolation used in Example 1. After confirming that the microorganisms grew sufficiently, the microorganisms were scraped off from the medium, and inoculated into the liquid medium for evaluation used in Example 1 to perform seed culture. After confirming that the microorganisms grew sufficiently by the seed culture, the microorganisms were inoculated into a 3-L jar fermenter. The composition of the medium in the 3-L jar fermenter was in accordance with Patent Document 9.

That is, a medium composed of sodium sulfate (12 g/L), KCl (0.5 g/L), MgSO$_4$.7H$_2$O (2 g/L), a defoamer Hodag K-60 (0.35 g/L), K$_2$SO$_4$ (0.65 g/L), KH$_2$PO$_4$ (1 g/L), (NH$_4$)$_2$SO$_4$ (1 g/L), CaCl$_2$.2H$_2$O (0.17 g/L), MnCl$_2$.4H$_2$O (3 mg/L), ZnSO$_4$.7H$_2$O (3 mg/L), CoCl$_2$.6H$_2$O (0.04 mg/L), Na$_2$MoO$_4$.2H$_2$O (0.04 mg/L), CuSO$_4$.5H$_2$O (2 mg/L), NiSO$_4$.6H$_2$O (2 mg/L), FeSO$_4$.7H$_2$O (10 mg/L), thiamine (9.5 mg/L), vitamin B12 (0.15 mg/L), and calcium pantothenate (3.2 mg/L) was prepared.

The changes were as follows: since the sugar consumption of the *Aurantiochytrium* sp. OH4 strain and LTR23 strain is high, the concentration of glucose was set to 120 g/L, and further, as the nitrogen source, a 28% NH$_4$OH solution was used. At a stage when the 120 g/L glucose in the medium was completely consumed, a glucose solution at a concentration of 65% was additionally fed to the medium, and the cultivation was continuously performed for up to 85 hours.

From the obtained culture, in the same manner as in Example 1, a lipid was extracted by the Bligh & Dyer method, followed by methylation, and the lipid was analyzed by gas chromatography.

The obtained microorganisms were frozen at −80° C., followed by lyophilization, whereby dried microorganisms were obtained. The weight of the thus obtained dried microorganisms was measured and converted into the original amount of the culture solution, whereby the dry cell weight (DCW) in the culture was calculated.

The results of the cultivation are shown in the following Table 2.

TABLE 2

Results of Cultivation in Jar Fermenter

|  | Unit | OH4 | LTR23 | SR21 | S31 |
|---|---|---|---|---|---|
| Dry cell weight | g/L | 145.3 | 133.8 | 118.3 | 90 |
| Content of DHA | g/L | 26 | 44 | 18 | 8.7 |
| DHA/total fatty acids | % | 27 | 52 | 26 | 44 |
| DHA productivity | g/L/hr | 0.294 | 0.505 | 0.211 | 0.402 |

As a result of cultivation, in the case of the *Aurantiochytrium* sp. OH4 strain, the dry cell weight was 145.3 g/L of the culture, and the content of DHA was 26 g/L of the culture, which resulted in significantly higher than in the case of the microorganisms having been reported as DHA high-producing microorganisms. Since DHA is accumulated in the microorganisms, a high dry cell weight has an advantage that the amount of DHA which can be finally collected is large.

Further, in the case of the *Aurantiochytrium* sp. LTR23 strain, the content of DHA was 44 g/L of the culture, the composition of DHA in the total fatty acids was 52%, and the DHA productivity was 0.505 g/L/hr, and thus, it was shown that the *Aurantiochytrium* sp. LTR23 strain surpasses the *Aurantiochytrium* sp. OH4 strain and the microorganisms having been reported as DHA high-producing microorganisms.

2. Composition of Fatty Acids in *Aurantiochytrium* sp. OH4 Strain and LTR23 Strain The compositions of fatty acids in the *Aurantiochytrium* sp. OH4 strain and LTR23 strain cultured in the jar fermenter are shown in the following Table 3. The values for the *Schizochytrium* sp. S31 strain were reprinted from Non-Patent Document 2.

TABLE 3

Composition of Fatty Acids

|  | OH4 | LTR23 | S31 (values in the document) |
|---|---|---|---|
| 12:0 | 1.9 | 1.8 | 0–0.5 |
| 14:0 | 5.1 | 1.4 | 9–15 |
| 16:0 | 59.8 | 26.3 | 24–28 |
| 16:1 | 0.3 | 0.3 | 0.2–0.5 |
| 18:0 | 1.7 | 1.1 | 0.5–0.7 |
| 20:3 (n-6) | 0.0 | 0.3 | 0–0.5 |
| 20:4 (n-3) | 0.9 | 0.3 | 0.5–1 |
| 20:5 (n-3) | 0.3 | 0.3 | — |
| 22:5 (n-6) | 4.4 | 16.0 | 11–14 |
| 22:6 (DHA) | 25.6 | 52.1 | 35–40 |

From the above results, it was shown that in the composition of fatty acids in the *Aurantiochytrium* sp. LTR23 strain, palmitic acid and short-chain saturated fatty acids decrease, and polyunsaturated fatty acids such as DHA and 22:5 (n-6) increase. It is known that saturated fatty acids increase LDL cholesterol and the ratio of the total cholesterol to HDL cholesterol, and it is pointed out that there is a possibility to increase the risk of diabetes. Therefore, also from the nutritional point of view, the significance of the *Aurantiochytrium* sp. LTR23 strain was shown.

3. Stability of *Aurantiochytrium* sp. LTR23 Strain

The *Aurantiochytrium* sp. LTR23 strain was obtained by introduction of a mutation, and therefore, there was a concern that the trait thereof is unstable. In light of this, the stability of the trait was examined by repeating subculture multiple times and performing cultivation in the same manner as in the above 1 using the subcultured strains. The results are shown in the following Table 4.

TABLE 4

Stability of *Aurantiochytrium* sp. LTR23 Strain

| Unit | Content of DHA (g/L) | DHA/total fatty acids (%) |
|---|---|---|
| First subculture | 47 | 52 |
| Second subculture | 37 | 51 |
| Third subculture | 41 | 53 |
| Fourth subculture | 44 | 51 |
| Fifth subculture | 44 | 52 |
| Average | 42.6 | 51.8 |
| Standard deviation | 3.8 | 0.8 |
| Coefficient of variation (%) | 8.9 | 1.6 |

The coefficient of variation was 10% or less in both of the production amount of DHA and the ratio of DHA, and therefore, it was shown that there is no problem in the stability of the *Aurantiochytrium* sp. LTR23 strain.

INDUSTRIAL APPLICABILITY

According to the present invention, a microorganism having a higher ability to produce DHA than before is provided. Also, efficient methods for producing a DHA-containing composition, DHA, and DHA alkyl ester using the microorganism are provided.

DESCRIPTION OF REFERENCE NUMERALS AND SIGNS

In FIGS. 1 and 3, the open circles (○) indicate DHA-producing microorganisms collected from a mangrove forest floor (a brackish water region) near a coastal area in Okinawa.

In FIG. 3, the closed square (■) indicates the *Aurantiochytrium* sp. LTR23 strain.

SEQUENCE LISTING FREE TEXT

SEQ ID NO: 6—Description of artificial sequence: Synthetic DNA

SEQ ID NO: 7—Description of artificial sequence: Synthetic DNA

The invention claimed is:

1. A method for producing a docosahexaenoic acid-containing composition, comprising culturing *Aurantiochytrium* sp. OH4 strain (Accession Number: FERM BP-11524) in a medium, allowing the docosahexaenoic acid-containing composition to be produced and accumulated in a culture, and collecting the docosahexaenoic acid-containing composition from the culture.

2. A method for producing docosahexaenoic acid comprising separating and collecting docosahexaenoic acid from the docosahexaenoic acid-containing composition collected according to claim 1.

3. A method for producing docosahexaenoic acid alkyl ester comprising separating and collecting docosahexaenoic acid alkyl ester from the docosahexaenoic acid-containing composition collected according to claim 1.

4. A method for producing docosahexaenoic acid alkyl ester according to claim 3, wherein the docosahexaenoic acid alkyl ester is docosahexaenoic acid methyl ester.

5. A method for producing docosahexaenoic acid alkyl ester according to claim 3, wherein the docosahexaenoic acid alkyl ester is docosahexaenoic acid ethyl ester.

* * * * *